United States Patent
Chinn et al.

(10) Patent No.: US 7,888,651 B2
(45) Date of Patent: Feb. 15, 2011

(54) METHOD AND SYSTEM FOR USING TISSUE-SCATTERED COINCIDENCE PHOTONS FOR IMAGING

(75) Inventors: Garry Chinn, San Mateo, CA (US); Craig S. Levin, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 58 days.

(21) Appl. No.: 12/154,261

(22) Filed: May 21, 2008

(65) Prior Publication Data

US 2009/0078876 A1   Mar. 26, 2009

Related U.S. Application Data

(60) Provisional application No. 60/931,177, filed on May 21, 2007, provisional application No. 60/931,178, filed on May 21, 2007.

(51) Int. Cl.
  *G01T 1/24* (2006.01)
(52) U.S. Cl. .................................. 250/370.13
(58) Field of Classification Search ........... 250/370.01–370.15; 378/98.8
  See application file for complete search history.

(56) References Cited

U.S. PATENT DOCUMENTS

| | | | |
|---|---|---|---|
| 6,303,935 B1 | 10/2001 | Engdahl et al. | |
| 2002/0008205 A1* | 1/2002 | Kurfess et al. | 250/370.13 |
| 2004/0081278 A1* | 4/2004 | Amemiya et al. | 378/63 |
| 2005/0207526 A1 | 9/2005 | Altman | |
| 2006/0131508 A1* | 6/2006 | Burr et al. | 250/370.11 |
| 2006/0138332 A1 | 6/2006 | Bryman | |
| 2009/0072156 A1 | 3/2009 | Chinn et al. | |
| 2009/0078876 A1 | 3/2009 | Chinn et al. | |

FOREIGN PATENT DOCUMENTS

WO  WO 2006/039494  4/2006

OTHER PUBLICATIONS

Wulf et al., "Germanium Strip Detector Compton Telescope Using Three Dimensional Readout," 2003, IEEE Nuclear Science Symposium Conference Record, vol. 1, pp. 57-61.*

(Continued)

*Primary Examiner*—David P Porta
*Assistant Examiner*—Kiho Kim
(74) *Attorney, Agent, or Firm*—Greer, Burns & Crain Ltd.

(57) ABSTRACT

Methods and systems for determining a location of a photon event for an imaging system including a plurality of 3-D detectors. For one of the photons in the photon pair, an interaction in a first 3-D detector is detected. For the other of the photons in the photon pair, at least two interactions in a second 3-D detector are detected. A cone-surface projector function is produced based on the at least two interaction locations in the second 3-D detector. A projector function is produced based on the produced cone-surface projector function, the detected interaction in the first 3-D detector, and the at least two detected interactions in the second 3-D detector.

19 Claims, 12 Drawing Sheets
(5 of 12 Drawing Sheet(s) Filed in Color)

OTHER PUBLICATIONS

Braem, Chamizo Llatas, Chesi, Correia, Garibaldi, Joram, Mathot, Nappi, Riberio da Silva, Schoenahl, Seguinot, Wieilhammer, and Zaidi, "Feasibility of a novel design of high resolution parallax-free Compton enhanced PET scanner dedicated to brain research," *Phys. Med. Biol.* vol. 49, 2547-2562 (2004).

Burdette, Chesi, Clinthorne, Honscheid, Huh, Kagen, Lacasta, Llosa, Mikuz, Park, Rogers, Studen, Weilhammer, "First Results from a Test Bench for Very High Resolution Small Animal PET using Solid-State Detectors," IEEE NSS-MIC, Puerto Rico, 2376-2380 (2005).

Chinn, G., Foudray, A., Levin, C., "Accurately Positioning and Incorporating Tissue-Scattered Photons into PET Image Reconstruction." 2006 IEEE Nuc. Sci. Symp. Conf. Rec., 1746-1751 (2006).

Chinn, G., Foudray, A., Levin, C., "A Method to Include Single Photon Events in Image Reconstruction for a 1 mm Resolution PET System Built with Advanced 3-D Positioning Detectors." 2006 IEEE Nuc. Sci. Symp. Conf. Rec., 1740-1745 (2006).

Chinn, G., Levin, C., "PET Image Reconstruction with a Bayesian Projector for Multi-Electronic Collimation Schemes." 2007 IEEE Nuc. Sci. Symp. Conf. Rec., 2799-2802 (2007).

Dogan, Wehe, and Akcasu, "A Source Reconstruction Method for Multiple Scatter Compton Cameras," IEEE Trans. Nuc. Sci., vol. 39, No. 6, 1427-1430 (1992).

Du, He, Knoll, Wehe, and Li, "Evaluation of a Compton scattering camera using 3-D position sensitive CdZnTe detectors," SPIE Conf. On Hard X-Ray, Gamma-Ray and Neutron Detector Physics, Denver, CO, SPIE vol. 3768, 228-238 (Jul. 1999).

Gillam, Beveridge, Lewis, "Positron Emission Imaging using Acquired Cone-Surfaces from Opposing Compton Cameras," 2004 IEEE Nuc. Sci Symposium Conf. Rec., vol. 5, 2810-2814 (2004).

Lehner, He, Zhang, "4πCompton Imaging using a 3-D Position-Sensitive CdZnTe Detector via Weighted List-Mode Maximum Likelihood," IEEE Trans. Nuc. Sci., vol. 51, No. 4, 3691-3694 (2004).

Parra, L., Barrett, H., "List-Mode Likelihood: EM Algorithm and Image Quality Estimation Demonstrated on 2-D PET." IEEE Trans. Med. Imaging, vol. 17(2), 228-235, Apr. 1998.

Singh, "An electronically collimated gamma camera for single photon emission computed tomography. Part I: Theoretical considerations and design criteria," Med. Phys., vol. 10(4), 421-427 (Jul./Aug. 1983).

Singh and Doria, "An electronically collimated gamma camera for single photon emission computed tomography. Part II: Image reconstruction and preliminary experimental measurements," Med. Phys., vol. 10(4), 428-435 (Jul/Aug 1983).

Tai, Laforest and Ruangma, "Design Study of a Detector Insert for High-Resolution Clinical PET Imaging," Conf Proc. IEEE NSS-MIC, Portland, 1714-1717 (2003).

Wilderman, Clinthorne, Fessler, Hua, Rogers, "List-Mode Maximum Likelihood Reconstruction of Compton Scatter Camera Images in Nuclear Medicine," Proceedings of the 1998 IEEE Nuclear Science Symposium, vol. 3, 1716-1720 (1998).

* cited by examiner

METHOD AND SYSTEM FOR USING TISSUE-SCATTERED COINCIDENCE PHOTONS FOR IMAGING

PRIORITY CLAIM AND REFERENCE TO RELATED APPLICATION

This application claims the benefit of U.S. provisional patent application Ser. No. 60/931,177, filed May 21, 2007, and U.S. provisional patent application Ser. No. 60/931,178, filed May 21, 2007, under 35 U.S.C. §119.

This application is also related to co-pending application Ser. No. 12/154,206, entitled "METHODS AND SYSTEMS FOR IMAGING", filed on even date herewith.

FEDERALLY-SPONSORED RESEARCH OR DEVELOPMENT

This invention was made with Government support under contracts EB003283 and CA119056 awarded by the National Institutes of Health. The Government has certain rights in this invention.

FIELD OF THE INVENTION

The invention relates generally to the field of high-resolution radiation imaging, and more particularly to methods and systems for imaging using positron emission tomography (PET).

BACKGROUND OF THE INVENTION

In tomography, measurements are taken through multiple views of a subject (e.g., human or animal in biomedical applications), and mathematical algorithms are used to convert these measurements into three-dimensional (3-D) images of the subject. Generally, in positron emission tomography (PET) and similar imaging methods, radioactive isotopes are injected into a subject. Decay of the isotopes (that is, a positron-electron annihilation event) results in photons being emitted from inside the animal.

In conventional PET, detectors positioned outside the animal detect emitted photon pairs when they hit the detectors. These interactions are recorded, including the particular detectors that are hit (the detection location) and the energy. Based on these recorded interactions, an image of where the radioactive isotope is distributed in the body can be imaged using a tomography image reconstruction algorithm.

Conventionally, emitted photon pairs from a source that are detected in coincidence by the detectors are used to reconstruct a 3-D tomographic image. True coincidence events are assumed to have occurred somewhere along the line between two photons detected within a preset coincidence time window. Thus, a line can be determined between the photon pair based on the location of the detected photos, and the determined lines are used to reconstruct the image using the tomography image reconstruction algorithm.

However, when a photon is scattered in tissue, such as in a Compton interaction, a scatter event occurs. Even when only one of the photons in a photon pair is scattered, producing so-called single scatter coincidence photons, the position of the annihilation event cannot be correctly localized. Thus, conventionally, the single scatter coincidence events are rejected using various techniques. For human patients, the scatter fraction is typically 50% of more of the coincidence events, resulting in the loss of significant amounts of information.

SUMMARY OF THE INVENTION

Embodiments of the present invention provide, among other things, a method and system for determining a location of a photon event for an imaging system including a plurality of 3-D detectors. The photon event produces a photon pair in coincidence. In an example method, for one of the photons in the photon pair, an interaction in a first 3-D detector is detected. For the other of the photons in the photon pair, at least two interactions in a second 3-D detector are detected. A cone-surface projector function is produced based on the detected interactions in the second 3-D detector. A projector function is then produced based on the produced cone-surface projector function, the detected interaction in the first 3-D detector, and the at least two detected interactions in the second 3-D detector.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 12A shows application of a line projector function for coincidence events with 450-570 keV energy, FIG. 12B shows application of a line projector function for scatter coincidence events with 300-450 keV energy (one photon underwent tissue scatter) at one detector and 450-570 keV energy at the other detector, and FIG. 12C shows application of an algorithm using a scatter projector function with a single iteration of 10 subsets applied to scatter coincidence events with a 300-450 energy window at one detector (where one photon underwent tissue scatter) and a 450-570 keV energy window at the other detector; FIG. 13A shows scatter coincidences within a 300-450 keV energy window, and FIG. 13B shows single events in a photopeak energy window (450-570 keV) using Compton kinematics collimation reconstruction.

DETAILED DESCRIPTION

Figure 1:
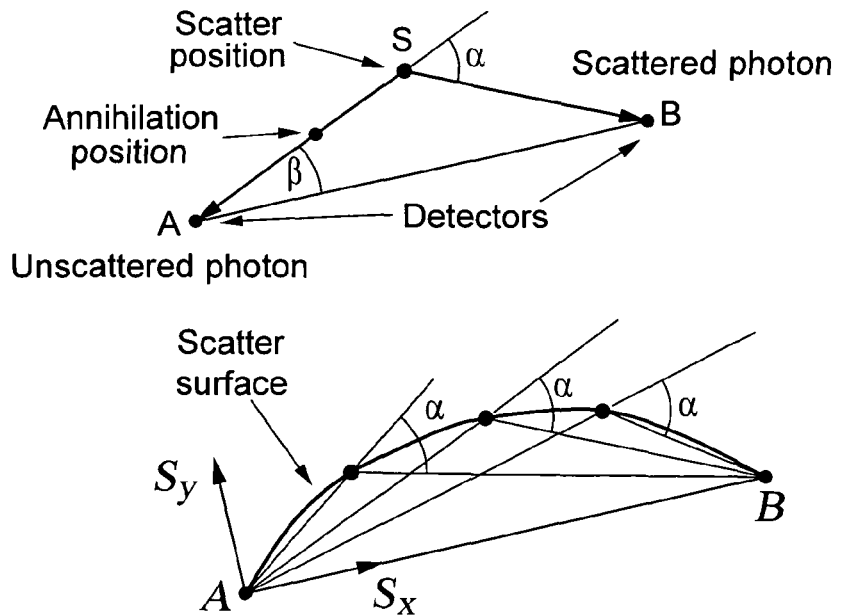
FIG. 1 is a diagram of a Compton scatter event in tissue.

True coincidence events may be used to provide imaging information by determining a line between a pair of detected photons, along which line an emission due to decay is determined to occur. However, the position of the radionuclide decay (i.e., where the emission occurred) cannot be determined for single scatter coincidence events using a conventional line projection function, because a line location cannot be determined. Thus, the information from the single scatter coincidence events is typically rejected. As used herein, with a single scatter coincidence photon event, two photons are detected in coincidence (e.g., at the same time, to a time resolution of electronics and detectors of a detection or imaging device or system), where one photon scattered once in tissue and the other photon did not scatter in tissue. True coincidence events occur when two photons are detected in coincidence, where neither photon is determined to have scattered in tissue. True coincidence events occur when two photons are detected in coincidence, where neither photon is determined to have scattered in tissue.

As single scatter coincidence photon events provide a significant amount of the overall photon events emitted, especially relative to true coincidence events, providing a method and system to consider these tissue-scattered photons has the capability to substantially improve the number of usable events (counts) in an imaging system such as a PET system. In turn, this can substantially improve the imaging statistics, potentially improving the sensitivity, image quality, and/or quantification.

Methods and systems of the present invention provide image reconstruction and detection that can use tissue-scattered coincidences to produce 3-D tomographic images. Example embodiments make use of Compton kinematics collimation, using individual interaction positions and energies, to identify the incident angle of single photons to localize the position of the decay event that generated the single scattered coincidence photons.

More particularly, example embodiments use a mathematical description of a new projector function that accurately positions a radionuclide decay event for single scatter coincidences. This single scatter projector function allows the decay position of single scatter coincidences to be accurately determined.

In an example method, multiple photon interactions (e.g., two) in a 3-D detector provide positions and energies that can be used to derive a cone-surface projector function, where the axis of the cone is determined by the spatial location of the multiple (e.g., two) interactions with a detector, and the measured energy of the interactions determines the angle of the cone. An example cone-surface projector function uses a Compton kinematics collimation. The Compton kinematics collimation may be performed for one or both of the detected coincidence photons. Using the Compton kinematics collimation for one or both photons, a scatter projector function can be defined, which may be used to determine a possible emission location.

Generally, in an imaging system including a plurality of 3-D detectors, methods are provided for determining a location of a photon event, where the event produces a photon pair. For one of the photons in the photon pair, an interaction is detected in a first 3-D detector and for the other of the photons in the photon pair, at least two interactions are detected in a second 3-D detector. The interaction for the first 3-D detector may be, for example, for a photon that is determined to not have been scattered in tissue, whereas the at least two detected interactions for the second 3-D detector may be, for example, for a photon that is determined to be scattered in tissue. The detected interaction in the first 3-D detector provides an interaction location and energy, and the at least two interactions for the second 3-D detector provide interaction location and energy for each of the at least two interactions.

The at least two interactions for the second 3-D detector occur in 3-D space within the second 3-D detector. A cone-surface projector function is produced based on the at least two detected interactions for the second 3-D detector. A single scatter projector function is then produced using the cone-surface projector function and detected interactions for the first 3-D detector and the second 3-D detector. For example, the detected interactions for the first 3-D detector and for the second 3-D detector (e.g., the first detected interaction in each of these detectors) can be used to produce a single scatter surface, which can be combined with the cone-surface projector function to provide the single scatter projector function.

The above imaging method may be augmented with a line projector function for true coincidence events to significantly increase a number of usable events. For example, within a predetermined time window, at least one signal can be received from each of a pair of 3-D detectors indicating a photon interaction. The combined energy of the at least one signal from the 3-D detectors in the pair can be determined, and compared to one or more energy windows. If the combined energy is within a first energy window, for example, it may be determined that a true coincidence event has taken place, and a line projector function may be generated based on the received at least one signal from the pair of 3-D detectors. If, on the other hand, the combined energy is within a second energy window, it may be determined that a scatter coincidence event has occurred, in which case a single scatter projector function may be produced, based on a cone-surface projector function.

An imaging system according to example embodiments of the present invention includes one or more detectors capable of measuring an interaction position (in three dimensions) and energies within the detectors of individual photons emitted from a source, and a device or system for image reconstruction coupled to the one or more detectors. Examples of sources of emitted photons will be known by those of ordinary skill in the art. A nonlimiting example source of emitted photons is animal tissue into which radioactive isotopes have been injected.

The one or more detectors include a plurality of detectors that are disposed to receive photons from a source of emitted photons and configured to generate a signal in response to a photon interaction. Such detectors may include, as nonlimiting examples, 3-D PET detectors and Compton cameras used in coincidence. Other suitable detectors capable of measuring the position (in three dimensions) and energies of individual photons emitted from the source may be used. Nonlimiting examples of PET systems include systems having 3-D positioning cadmium-zinc-telluride (CZT) detectors. An example CZT detector that may be used is described in International Patent Application No. PCT/US2005/035203, filed Sep. 30, 2005, which is incorporated in its entirety by reference herein.

Example embodiments of the present invention use CZT detectors having three-dimensional positioning capabilities for high-resolution PET imaging. Example detectors exhibit high spatial resolution (e.g., 1 mm), energy resolution (e.g., 2.5% full width at half maximum for 511 keV photons), and the ability to identify the 3-D coordinates of individual Compton and photoelectric interactions within the detector. Such detectors can operate in a conventional PET mode, as will be appreciated by those of ordinary skill in the art, measuring photons in coincidence, but also as a Compton camera for single photon events. Such capabilities can be used to reconstruct tissue-scatter coincidence events according to example methods of the present invention.

An image generator, that is a device or system for image reconstruction, is configured to produce a cone-surface projector function based on at least two interaction signals from one of a pair of the 3-D detectors, and a single-scatter projector function based on the cone-surface projector function as well as an interaction signal from each of the pair of 3-D detectors. In this way, the image generator is configured to generate images using data from scatter coincidence events. Such an image generator preferably is configured to generate a plurality of single-scatter projector functions and generate an image based on the plurality of single-scatter projector functions. Further, the image generator may be further configured to produce a line projector function for true coincidence events, for example based on interaction signals from each of a pair of the 3-D detectors. Such interaction signals include, for example, signals indicating interaction location and energy.

Examples of image generators include a computing device (as a nonlimiting example, a personal computer (PC) or a group of connected PCs) suitable for running an image reconstruction algorithm, which may be implemented in software, hardware, firmware, loaded via suitable media, etc. A computing device may include a suitable processor(s), memory, input devices, storage devices, output devices (such as, but not limited to, printers, monitors, network outputs, etc.) coupled to one another via a bus or other suitable connection and be configured to receive inputs directly or indirectly from the one or more detectors via any suitable connection. According to example embodiments of the present invention, the computing device is configured to implement an image reconstruction algorithm. Thus, additional embodiments of the present invention may be provided in a computing device configured to perform methods of the present invention and/or a computer-readable medium, a propagated signal, firmware, software, etc. capable of causing a computing device to perform a method of the present invention.

It will be appreciated that various PET systems, including various commercial PET systems, capable of 3-D positioning may be used as the one or more detectors and the image generator if configured to implement example image reconstruction algorithms according to the present invention. Generally, the effectiveness of any such system will at least partly depend on the 3-D positioning resolution and energy resolution of the detectors used.

Preferred embodiments will now be discussed with respect to the drawings. The drawings include schematic figures that are not to scale, which will be fully understood by skilled artisans with reference to the accompanying description. Features may be exaggerated for purposes of illustration. From the preferred embodiments, artisans will recognize additional features and broader aspects of the invention.

Principles of embodiments of the present invention will now be explained. In a Compton camera, the kinematics of Compton scatter in the detector is used to determine the incident direction of the detected photons. A PET method using this principle may be referred to as Compton kinematics PET. A Compton camera typically includes a scattering layer and a photoelectric absorption layer. The position and energy deposited by a Compton interaction in the scattering layer is measured, along with the position and energy of the interaction in the absorption layer. The direction of the photon can be electronically collimated to a cone surface. Therefore, Compton kinematics PET does not require photons to be detected in pairs.

In both conventional and Compton kinematics PET, a photopeak energy window is used to help select those pairs of photons that have not been scattered by tissue. A non-scattered coincidence photon event may be referred to as a true event (a "true"). If one photon is scattered in tissue by a Compton interaction, the position of the annihilation event cannot be correctly localized. This type of event may be referred to as a scatter event.

Example methods of the present invention allow reconstruction of images from photons that have undergone a single Compton scatter interaction in tissue, so-called scatter coincidence photon events. Example image reconstruction methods are applicable to any type of PET system capable of both coincidence detection and Compton kinematics imaging.

In PET, the projector function for a true coincidence is a line between two detectors. According to embodiments of the present invention, a single-scatter projector function is provided that corresponds to coincidence events when one of the detected photons has been scattered a single time in tissue and the other detected photon has not undergone any scatter.

FIG. 1 depicts Compton scatter in tissue. The positron-electron annihilation occurs along the line segment $\overline{AS}$. One photon is not scattered in tissue (a so-called "true" photon) and is detected at position A, which may be, for example, the position of the first interaction at a first detector. The second photon (a so-called "scatter" photon) is scattered at the point S at an angle α (angle between $\overline{AS}$ and $\overline{SB}$) and is detected in coincidence at position B, which may be, for example, the position of the first interaction at a second detector. Using $E_b$, the energy measured at B, the angle α is calculated by the Compton scattering formula as $$\cos\alpha = 1 - m_e c^2 \left( \frac{1}{E_b} - \frac{1}{E_{511}} \right). \qquad (1)$$

Figure 2:
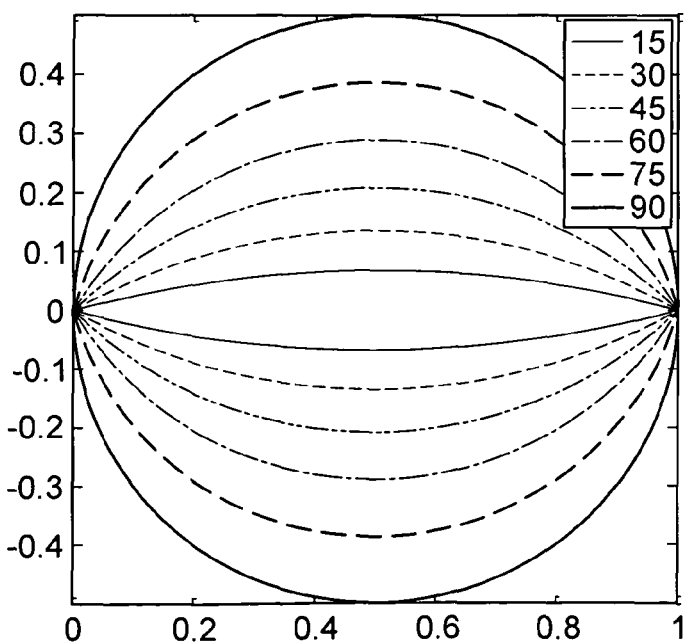
FIG. 2 is a two-dimensional plot of a scatter surface for various scatter angles in tissue.

The photon is scattered somewhere along a football-shaped surface shown as the shaded line rotated about the line segment $\overline{AB}$ in FIG. 1. This line is referred to herein as the single scatter surface, a two-dimensional plot of which is shown by example in FIG. 2. In FIG. 2, let A lie at the origin (0,0) and B lie on the x-axis at x=D. The single scatter surface is then described as the set of points $(s_x, s_y)$, wherein $$s_x = \frac{D \tan(\alpha - \beta)}{\tan(\alpha - \beta) + \tan\beta} \qquad (2)$$

$$s_y = s_x \tan\beta$$

where β is the angle between $\overline{AS}$ and $\overline{AB}$. For an arbitrary line segment $\overline{AB}$ that does not lie on the x-axis, apply a rotation and translation transformation to arrive at the coordinate frame of $(s_x, s_y)$.

The positron-electron annihilation event occurs somewhere between point A and the point where the photon scattered in tissue, hence the annihilation could have occurred anywhere within the volume enclosed by the single scatter surface. Suppose that the photon scattered at position S in FIG. 1. The probability that the positron-electron annihilation occurred on the line segment $\overline{AS}$ is not uniform for all points S on the scatter surface. Let l and m denote the lengths of the segments $\overline{AS}$ and $\overline{AB}$, respectively. For uniform linear attenuation coefficient μ, the probability that the emission occurred along line segment $\overline{AS}$ is $$p(as) = e^{-\mu(l+m)}. \tag{3}$$

The scatter projector function may thus be calculated by using equation (2), a translation and rotation operation to the line segment $\overline{AB}$, and application of equation (3).

The envelope of the single scatter surface is plotted as a function of the scatter angle in FIG. 2. For low angle tissue scatter, the annihilation event occurs somewhere near the line of response between the coincident detector pair. Generally, the position of the annihilation event cannot be precisely localized. As a nonlimiting example, in the scatter surface show in FIG. 2, at small scatter angles, such as 15 degrees, the line of response reasonably approximates the projector function. For a large scatter angle, such as 90 degrees, the photon could have originated anywhere within the field of view.

Figure 3:
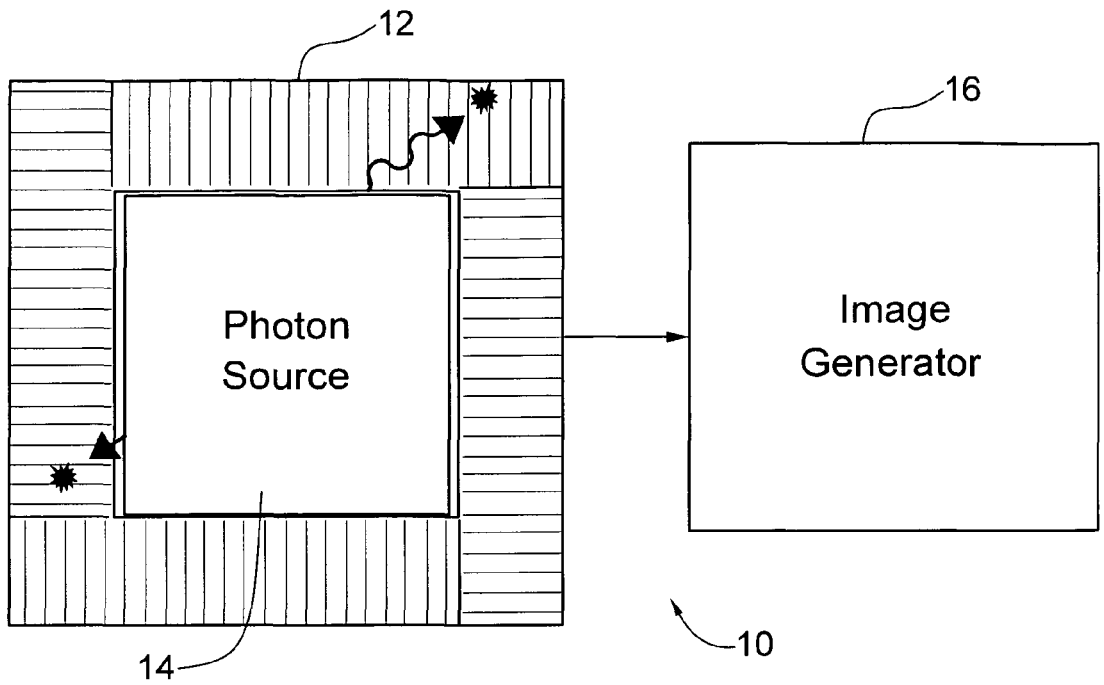
FIG. 3 illustrates an imaging system according to embodiments of the present invention.

FIG. 3 shows an example imaging system 10. The imaging system 10 includes a plurality of 3-D detectors 12 disposed with respect to a source 14 of emitted photons. These 3-D detectors 12 are suitably coupled to an image generator 16, which receives signals from the 3-D detectors and processes the signals to generate an image. Examples of suitable couplings will be understood by those of ordinary skill in the art, including but not limited to electrical and optical couplings. Examples of suitable image generators 16 are described above. It is not required that the image generator 16 be co-located with the 3-D detectors, but may be located anywhere that signals from the 3-D detectors may be received.

To practically reconstruct scatter coincidence events, a 3-D detector should be capable of efficient coincidence detection and Compton kinematics. Thus, traditional Compton cameras are not ideal. However, 3-D positioning cadmium zinc telluride (CZT) detector modules, such as but not limited to those disclosed in International Patent Application No. PCT/US2005/035203, filed Sep. 30, 2005, can be used for tissue-scatter coincidence image reconstruction according to example embodiments of the present invention. Compton cameras used in coincidence may be used as well.

Figure 4:
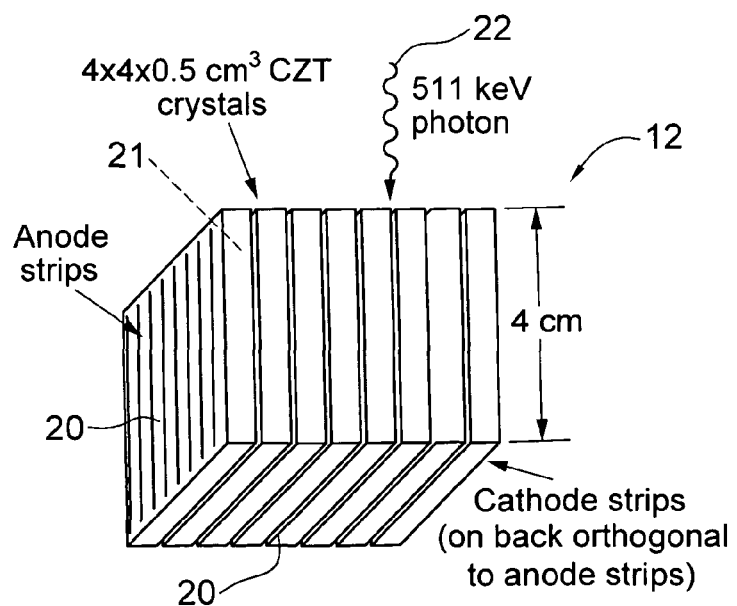
FIG. 4 shows an example cadmium zinc telluride (CZT) detector, according to embodiments of the present invention.

CZT is a semiconductor that directly converts incident high-energy photons into electrical signals. For example, as shown in FIG. 4, orthogonal anode and cathode cross strips 20 on a CZT crystal 21 are used to sample the interaction position of a photon 22 along two dimensions. The position of the interaction in the third dimension is computed from the anode-to-cathode signal ratio. A 1 mm×1 mm×1 mm spatial resolution can be achieved by using 1 mm pitch anode and cathode cross strips. The energy resolution has been measured at ≦2.5% FWHM for 511 keV photons. These example CZT detectors are then stacked in an edge-on configuration (FIG. 3) to provide high intrinsic detection efficiency and facilitate coupling to readout electronics. With a minimum photon travel distance of 4 cm, the single photon detection efficiency is 86% (74% for coincident photons).

Figure 5:
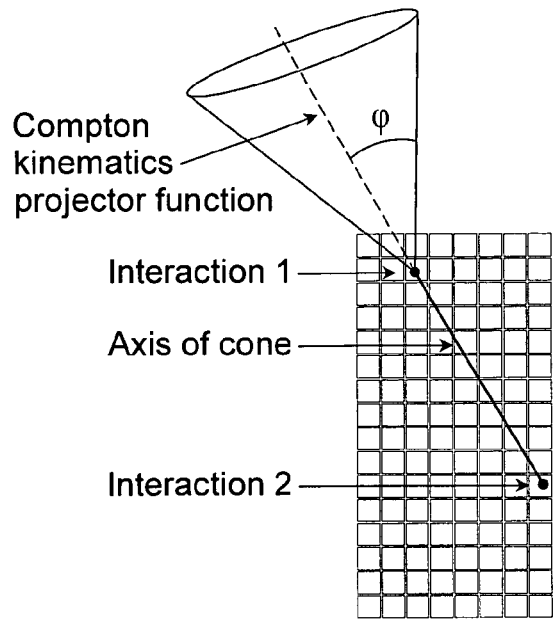
FIG. 5 illustrates Compton kinematics for a 3-D detector, wherein the spatial location of two interactions in the detector determines the axis of a cone, and the measured energy of the interactions determines the angle of the cone.

FIG. 5 illustrates how a high-resolution 3-D detector can estimate the incident angle of a single detected photon. The incident angle of the photon can be calculated when the position and energy of the first two interactions in the detector are measured. Monte Carlo simulations suggest that 70% of all detected events involve two or more interactions in the detectors.

A cone-surface projector function is formed for the single photon where the line formed by the two interactions from the cone axis and the cone half angle φ is calculated by $$\cos\varphi = 1 - m_e c^2 \left( \frac{1}{E_1} - \frac{1}{E_0} \right) \tag{4}$$

where $E_0$ is the incident photon energy and $E_1$ is the photon energy after the first Compton interaction in the detector, $m_e$ is the mass of an electron, and c is the speed of light. Doppler broadening, energy blurring, and spatial blurring in the 3-D detector leads to angular blurring of the cone half angle φ.

Using only the tissue scattering angle α (FIG. 1), the positron-electron annihilation event could have occurred anywhere inside a football-shaped region. However, by using the kinematics of Compton scattering (Compton kinematics) for a photon that has two or more interactions in a high-resolution 3-D positioning PET detector, the localization of the positron-electron annihilation position can be improved.

Figure 6A:
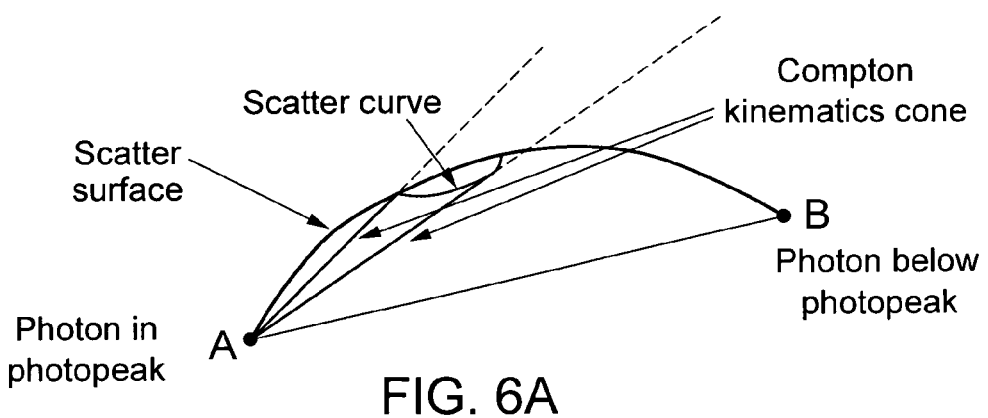
FIGS. 6A-6B show examples of a single-scatter projector function when Compton kinematics is performed only for an unscattered photon.
Figure 6B:
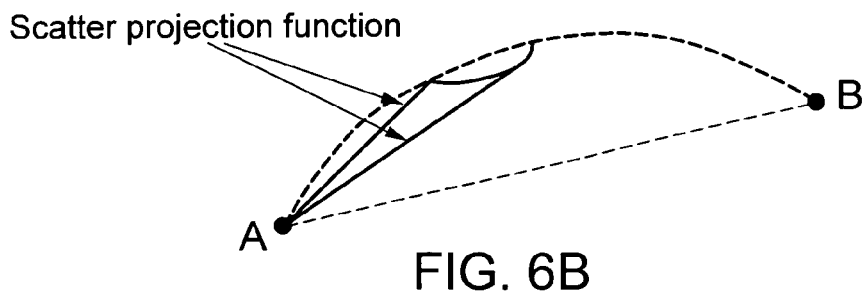

FIGS. 6A-6B show examples of a single-scatter projector function when Compton kinematics is performed only for an unscattered photon. In FIG. 6A, Compton kinematics is performed at detector A (where the unscattered photon was detected), producing the Compton kinematics projector function (a conical surface) shown. The locus of points where the photon scattered can now be further constrained from the single scatter surface to the intersection of the single scatter surface and the detector Compton kinematics cone surface. This intersection is shown as a closed curve. The annihilation event must lie somewhere between detector A and the scatter locus, and this defines the single scatter projector function, which is shown as a cone in FIG. 6B.

Figure 7A:
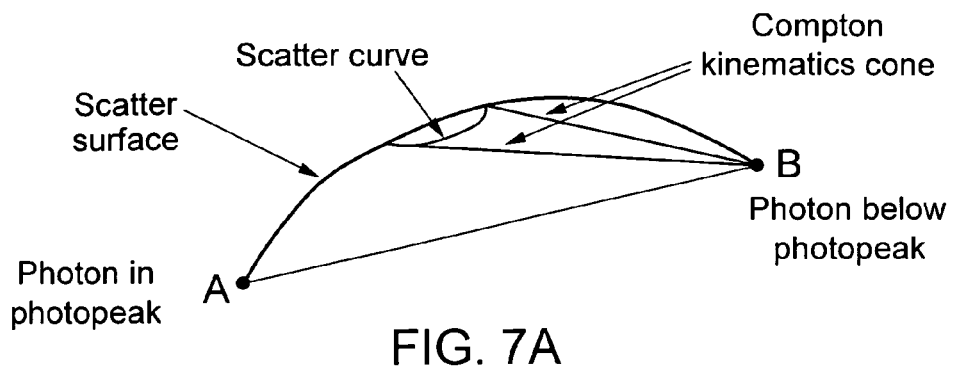
FIGS. 7A-7B show examples of a single-scatter projector function when Compton kinematics is performed only for a scattered photon.
Figure 7B:
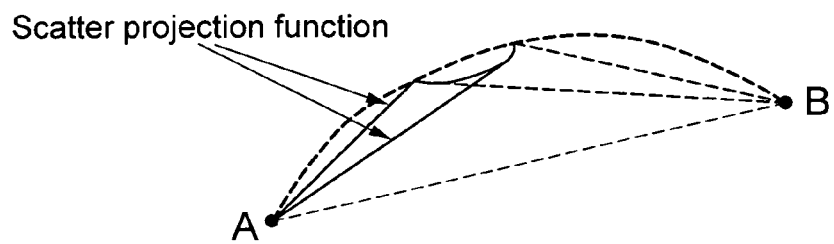

FIGS. 7A-7B show the case when Compton kinematics is performed only for the scattered photon. An unscattered photon is detected at detector A and the single-scattered photon at detector B. The scatter projector function is derived in similar fashion to FIGS. 6A-6B, and is shown in FIG. 7B. The scatter surface is shown with the detector Compton kinematics cone-surface projector for detector B. The photon is known to have scattered at the intersection of the single-scatter surface and the Compton kinematics cone-surface. This closed curve, a cone, is shown in FIG. 7B. The photon annihilation must have occurred somewhere between detector A and the scatter curve producing the single scatter projector function shown.

Figure 8A:
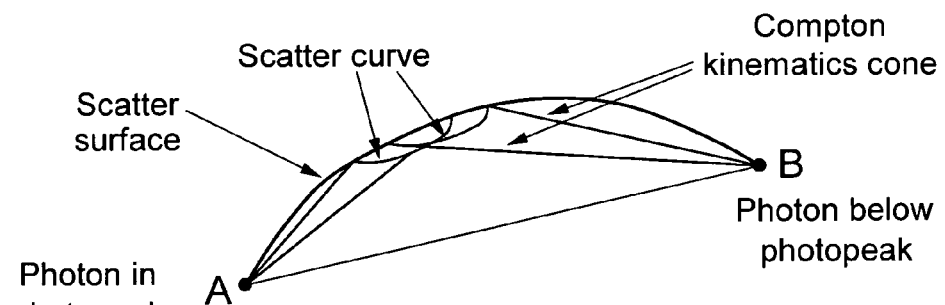
FIGS. 8A-8B show examples of a single-scatter projector function when Compton kinematics is performed for a first detector (an unscattered photon) and for a second detector (a scattered photon)
Figure 8B:
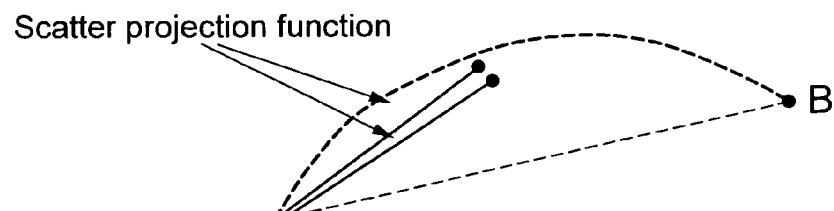

FIGS. 8A-8B show the case when Compton kinematics is performed in both detectors. The scatter surface is shown with the detector Compton kinematics cone-surface projector for both detectors. Now, the locus of points where the scatter occurred in tissue is the intersection of the two Compton kinematics cone surfaces and the single scatter surface. This intersection can be a single point, a pair of points or a closed curve like those shown in FIGS. 6A-6B and 7A-7B. The most common case will be a pair of points as shown in FIG. 8B. The photon annihilation must have occurred somewhere between detector A and the scatter locus (shown in FIG. 8B as two points, the most common case) producing the single scatter projector function shown, which includes a pair of lines.

Figure 9:
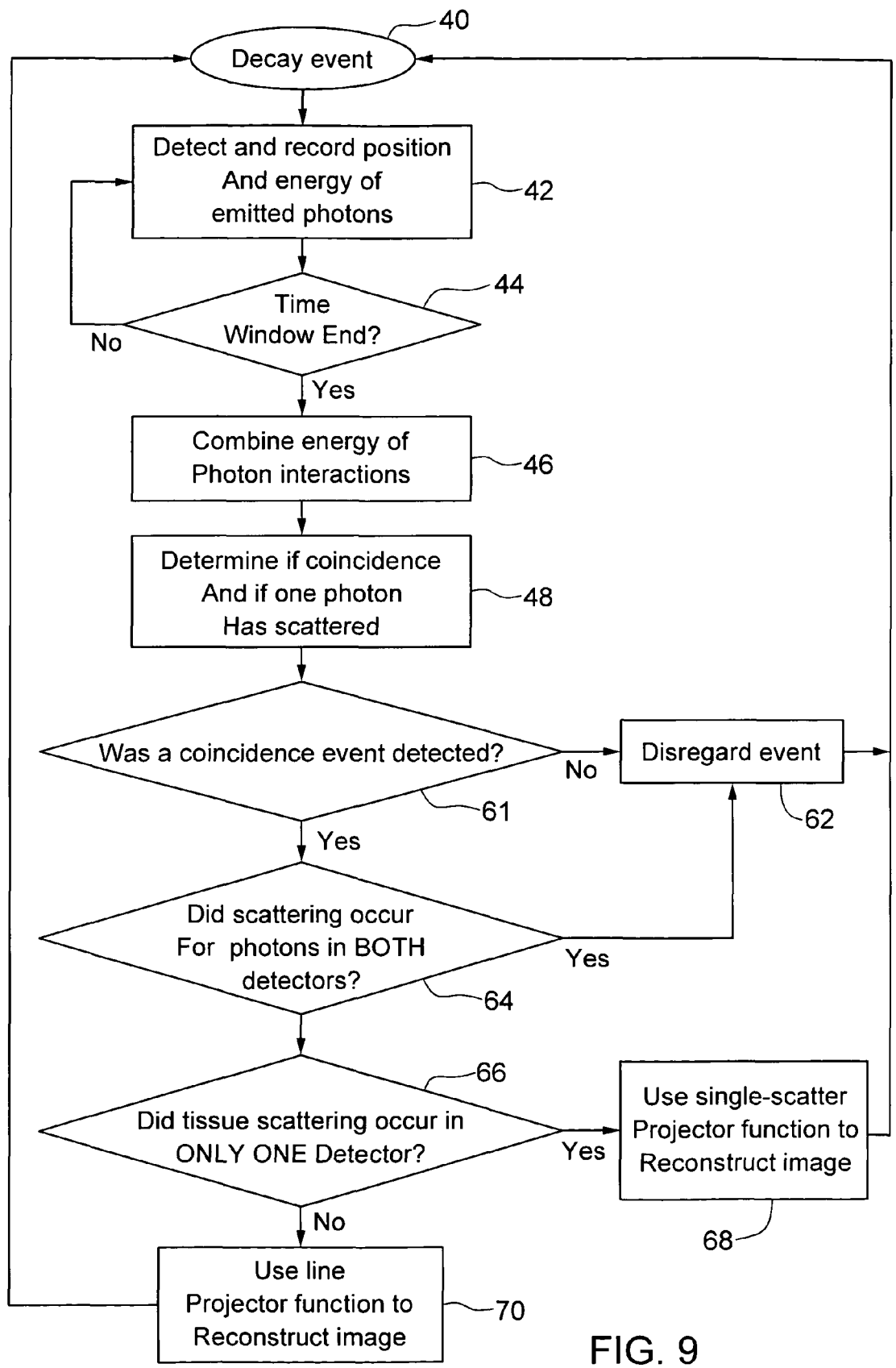
FIG. 9 shows an example imaging method, according to embodiments of the present invention.

FIG. 9 shows an example imaging method for embodiments of the present invention based on the projector functions described above. In an example imaging method, for a decay event (step 40), measured using a preset coincidence time window, emitted photons are detected (step 42) as photon interactions with the one or more detectors, and at least one position (individual location) and energy of interaction is recorded. When the time window is completed (step 44), the energy of recorded photon interactions within the time window is combined (step 46) (as a nonlimiting example, summed), and a determination is made (step 48) as to whether a photon pair (i.e., a coincidence) has been detected and if so, whether one of the detected photon pair is scattered.

Figure 10:
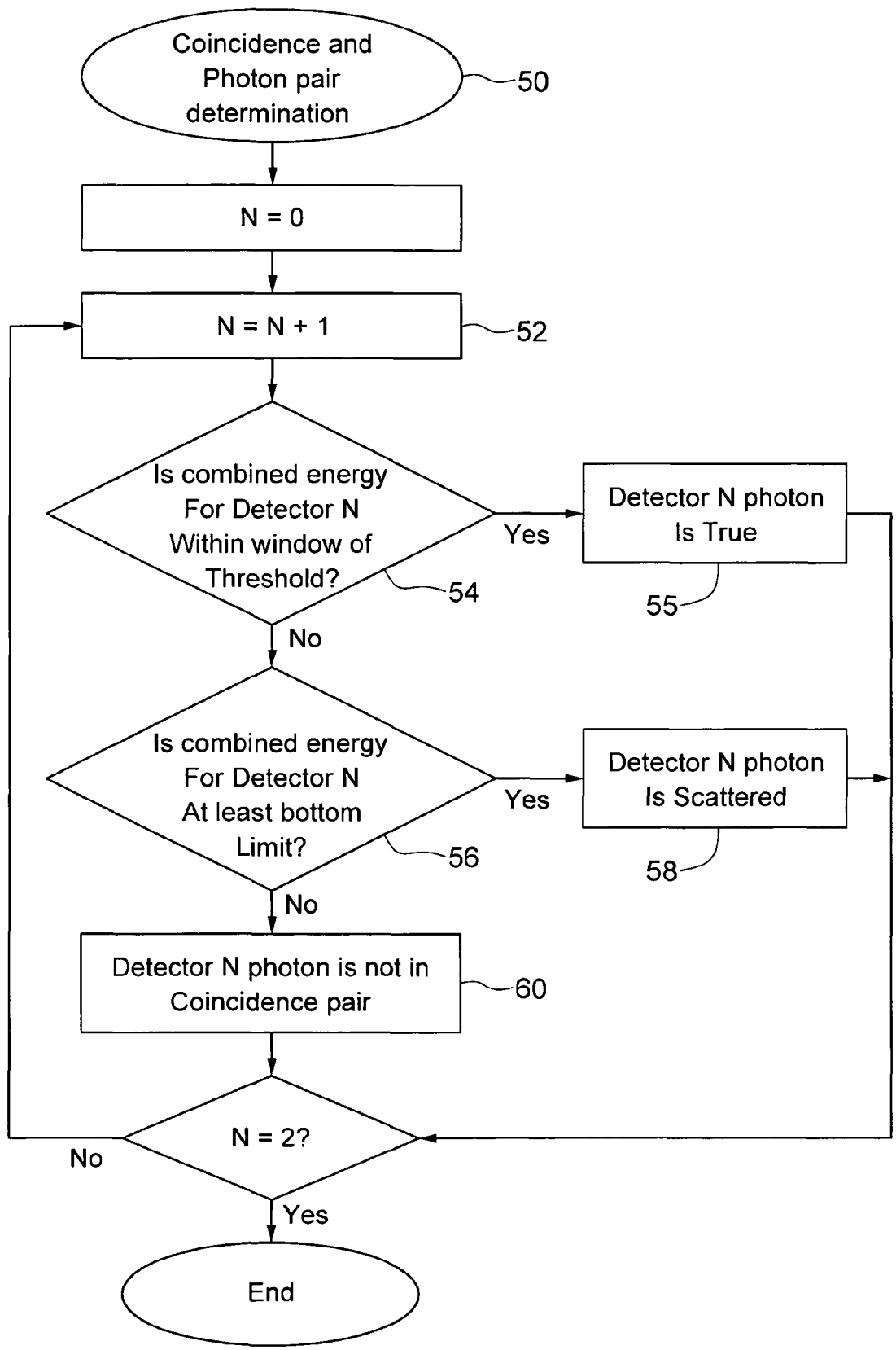
FIG. 10 shows an example method for determining whether a true coincidence event or a scattered coincidence event is present.

Preferably, as shown in FIG. 10, the determination is based on the combined amount of interaction at a particular detector location within the time window, by comparing (step 50) the energy to a threshold. As a nonlimiting example, within the time window, photon interaction may take place at two distinct detector locations. For each detector (step 52), if the combined photon interaction energy at a particular location is 511 keV, or within a window surrounding 511 keV (step 54), it is determined (step 55) that tissue scattering did not occur for that photon; i.e., that the photon is true. If the combined photon interaction energy is below the threshold or window, but at least a bottom limit (step 56) it is determined (step 58) that tissue scattering did occur for that photon. If the combined energy for the detector is below the bottom limit (step 60), the photon for the detector is not considered part of a detected coincidence pair.

Referring again to FIG. 9, if a coincidence event is not detected (step 61) (for example, because a photon for one of the detectors was below a bottom limit), the event may be disregarded (step 62). If both photons in the pair are determined to have scattered in tissue (step 64), then the information also may be disregarded (step 62).

If tissue scattering did occur for one photon of the photon pair, but not for the other photon (step 66), it is determined that single scattered coincidence photons are present, and a single scatter projector function is used to update the image (step 68). For determined single scattered coincidence photons within the time window, the three-dimensional position and interaction energy (or energies) for each of the photons is input to the image reconstruction algorithm to provide a single-scatter projector function such as that described above.

If tissue scattering did not occur for either photon of a detector photon pair, then a suitable method, such as but not limited to a standard line projector function (step 70), may be used to determine the emission location and update the image. For example, a series of lines may be determined using the line projector function, each providing a probability of an emission location. The intersection of these lines may be determined to be the emission location.

An example method then waits for the next decay event, and again records events. An image may be reconstructed over several decay events using the example method illustrated in FIGS. 9 and 10.

As a nonlimiting example of an image reconstruction algorithm, the list-mode ordered subset expectation maximization (LM OS-EM) algorithm can be used to reconstruct images by incorporating the line projector function and single scatter projector function according to embodiments of the present invention. LM OS-EM is described, for example, in S. J. Wilderman, N. H. Clinthorne, J. A. Fessler, C-H Hua, and W. L. Rogers, "List mode EM reconstruction of Compton scatter camera images in 3-D," *Proceedings of the* 1998 *IEEE Nuclear Science Symposium*, vol. 3, pp. 1716-1620, 1998; and H. M. Hudson and R. S. Larkin, "Accelerated image reconstruction using ordered subsets of projected data," *IEEE Trans. Med Imaging*, vol. 13, pp. 601-609, 1994. Other image reconstruction methods are possible, including but not limited to sinogram-based, histogram-based, list-mode, etc.

The list-mode expectation algorithm (EM) can be used to reconstruct the image with voxels $\lambda_j$ using the iteration $$\lambda_j^{l+1} = \frac{\lambda_j^l}{n_j} \sum_i \frac{m_i p_{ij}}{\sum_k p_{ik} \lambda_k^l} \quad (5)$$

where l is the previous iteration number, $n_j$ represents the sensitivity correction for the j-th voxel, and $p_{ij}$ represents the discrete weights of the projector function for the j-th voxel and measurement $m_i$. If $m_i$ is a scatter event and Compton kinematics is performed at one or both detectors, then $p_{ij}$ is calculated from the discrete version of the scatter projector function. Otherwise, $m_i$ is a true coincidence event, and the standard line projector function is used for $p_{ij}$.

Ordered subsets are used to accelerate the image reconstruction process by dividing the list-mode data set into S data sets with an equal number of counts. The image is then updated after each subset before the next data subset is processed. Each iteration pass through the entire data set then results in S image updates, accelerating the reconstruction process.

Simulation

Figure 11:
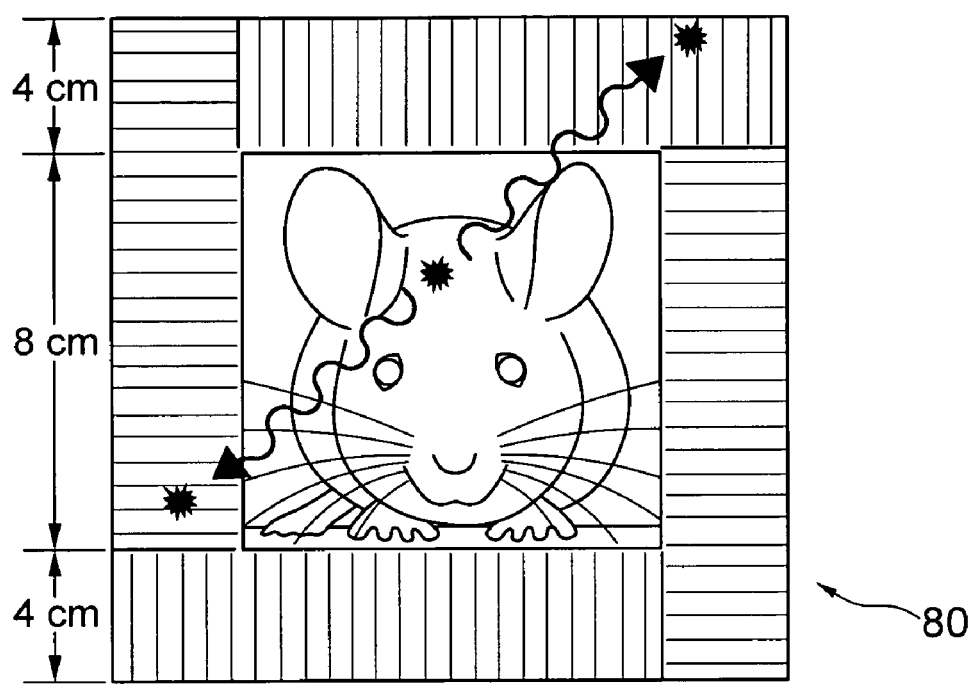
FIG. 11 shows an example imaging system according to an embodiment of the invention.

Simulations of PET systems built using CZT detectors were performed. A Monte Carlo simulation package was used to simulate a phantom for an 8×8×8 cm³ FOV box-shaped small animal PET system built using the 3-D positioning CZT detectors. It was assumed that the detectors had a 1×1×1 mm³ spatial resolution with 2.5% energy resolution for 511 keV photons. It was also assumed that the energy resolution FWHM was $3\% * \sqrt{511/e_{pho}}$, where $e_{pho}$ is the energy of the photon in keV. A schematic of this system 80 is shown in FIG. 11. The Monte Carlo simulation was used to generate hits files of all the individual interactions within the detectors. These files were processed to simulate the energy and spatial resolution performance of the example 3-D detector system.

As a demonstration, data was first simulated for ideal detectors. A phantom of 3 spherical sources with 3 mm diameter was simulated in a 5 cm diameter cylinder of water with no background activity for an 8 cm×8 cm×8 cm FOV box-shaped small animal PET system. A 450-570 keV energy window was used to reject tissue-scattered photons, and a 300-450 keV energy window was used to acquire photons that scattered in tissue. The fully 3-D list-mode ordered subset expectation maximization (3D OS-EM) algorithm was used with two different projector functions: the standard line projector function and the scatter projector function. In producing the scatter projector function, exactly one of the detectors was configured to receive two or more interactions, and a cone-surface projector function was produced for that detector. Depending on whether or not the photon interacting with that detector was scattered in tissue, the first or second example single scatter projector functions were used.

Figure 12A:
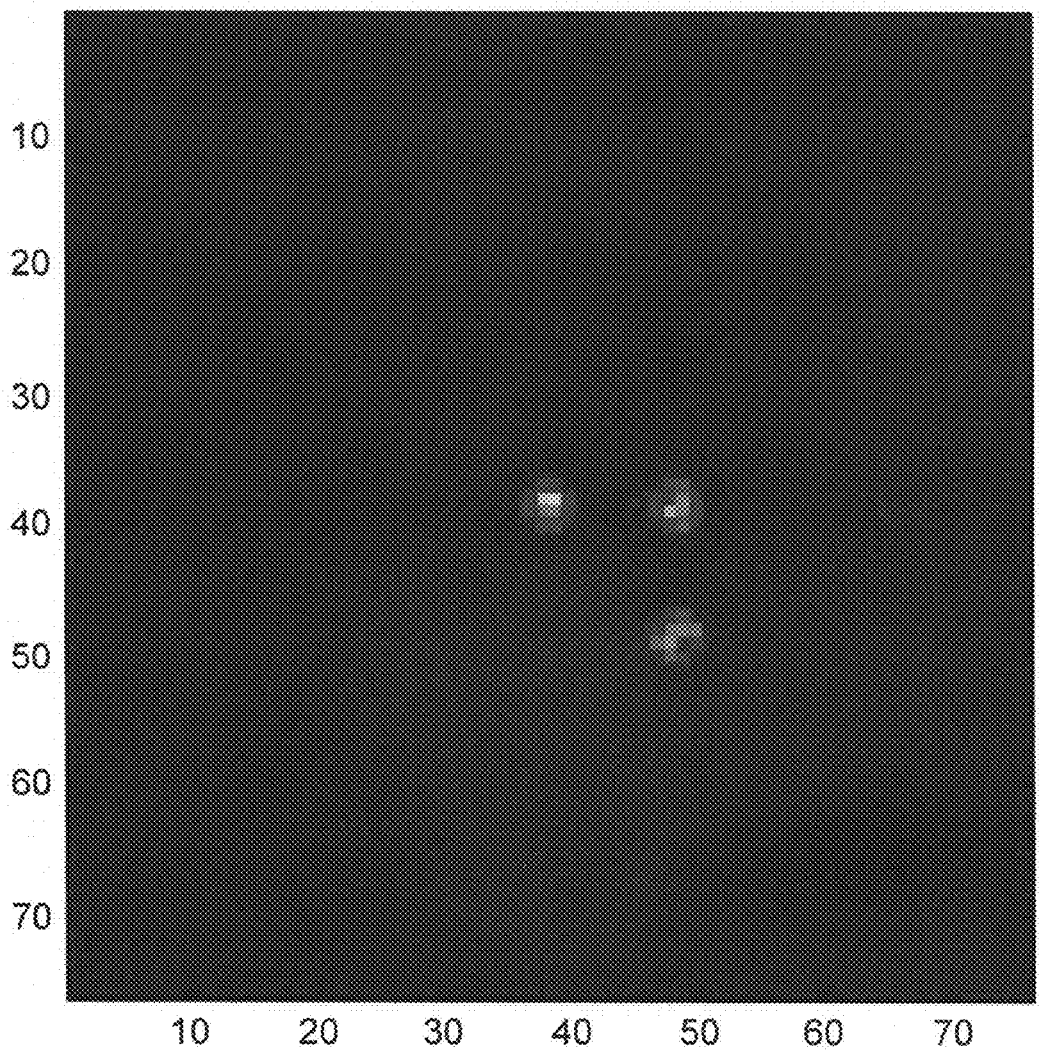
FIGS. 12A-C show images reconstructed for a phantom with 3 mm spherical sources in a 5 cm diameter water-filled cylinder, according to an example method of the invention, where
Figure 12B:
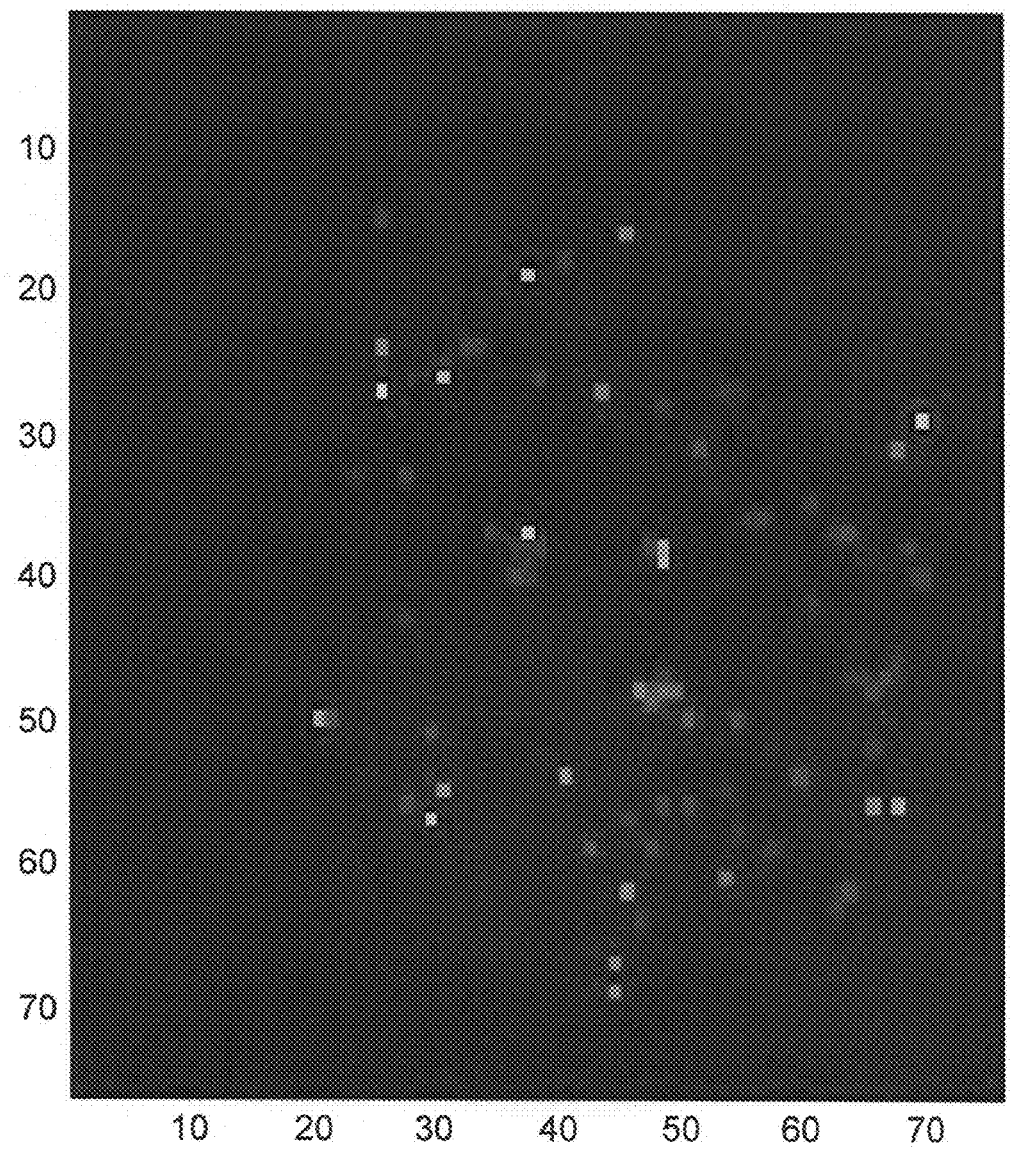
Figure 12C:
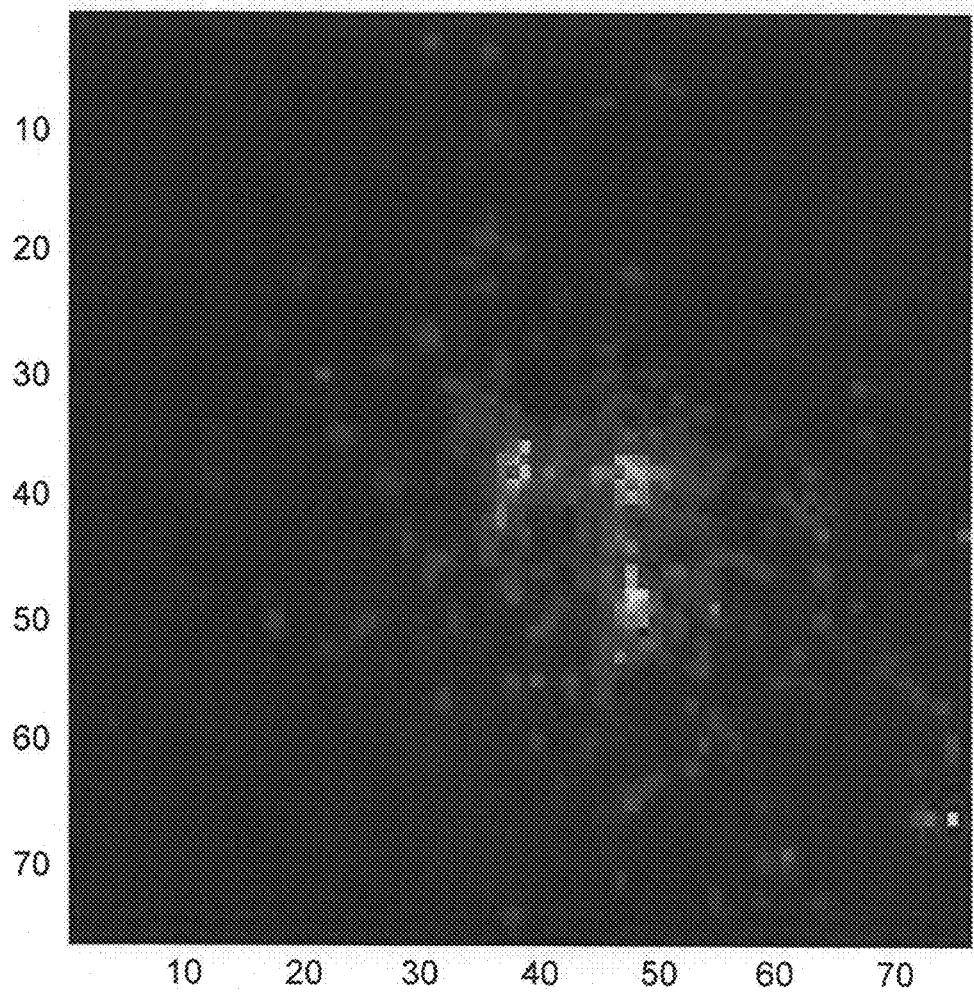

FIGS. 12A-C show the results produced by a single iteration with ten subsets of the LM OS-EM algorithm. It is shown that the line projector function only works when both photons are between 450-570 keV (FIG. 12A). When the energy of one of the observed photons is 300-450 keV (underwent tissue scatter) and the second photon energy is 450-570 keV, the standard line projector cannot recover the original activity distribution (FIG. 12B). The scatter projector function can successfully recover the activity distribution when one photon has energy within 300-450 keV (tissue scatter) and the second photon has energy within 450-570 keV (FIG. 12C). The reconstructed resolution of the 3 mm diameter spheres for unscattered events was approximately 3.0 mm full width at half maximum (FWHM). When one photon has been scattered in tissue, the recovered tissue scatter data had approximately 4.0 mm FWHM spheres for detectors with perfect energy and spatial resolution. By using both the standard line projector function along with the scatter projector function, the energy window can be opened up wider, substantially increasing the overall sensitivity of the system.

Next, for resolution comparison with singles imaging, detectors with energy blurring and spatial positioning blurring were simulated. Practical scatter coincidence reconstruction uses Compton kinematics collimation at one or both detectors. The reconstructed spatial resolution is dependent on the angular resolution of the Compton camera. Consequently, the spatial blurring increases with distance from the detector.

Compton kinematics collimation can be used to reconstruct single photon events. In this case, the cone-surface projector function extends across the field of view (FOV). The scatter projector function also has a cone-surface shape, but it only extends to the single scatter surface, and is therefore expected to produce images with better spatial resolution then Compton collimation would produce for single photon events.

This expectation was confirmed by simulating a resolution phantom that was a 5 cm diameter, water-filled cylinder with a single plane of spherical sources divided into four quadrants. The spherical sources in each quadrant were 1, 1.25, 1.5, and 1.75 mm in diameter with center-to-center separation that was twice the diameter of the spheres. Activity of 0.2 mCi was simulated in the small animal system with a 2 cm axial length.

Figure 13A:
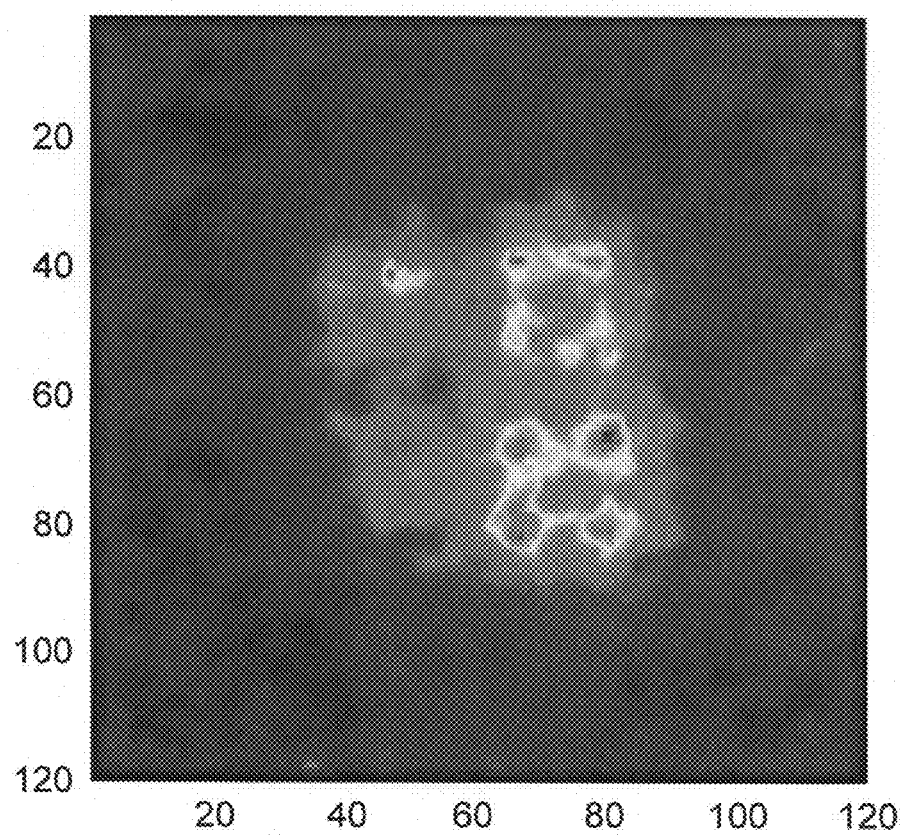
FIGS. 13A-13B show reconstructed images, where
Figure 13B:
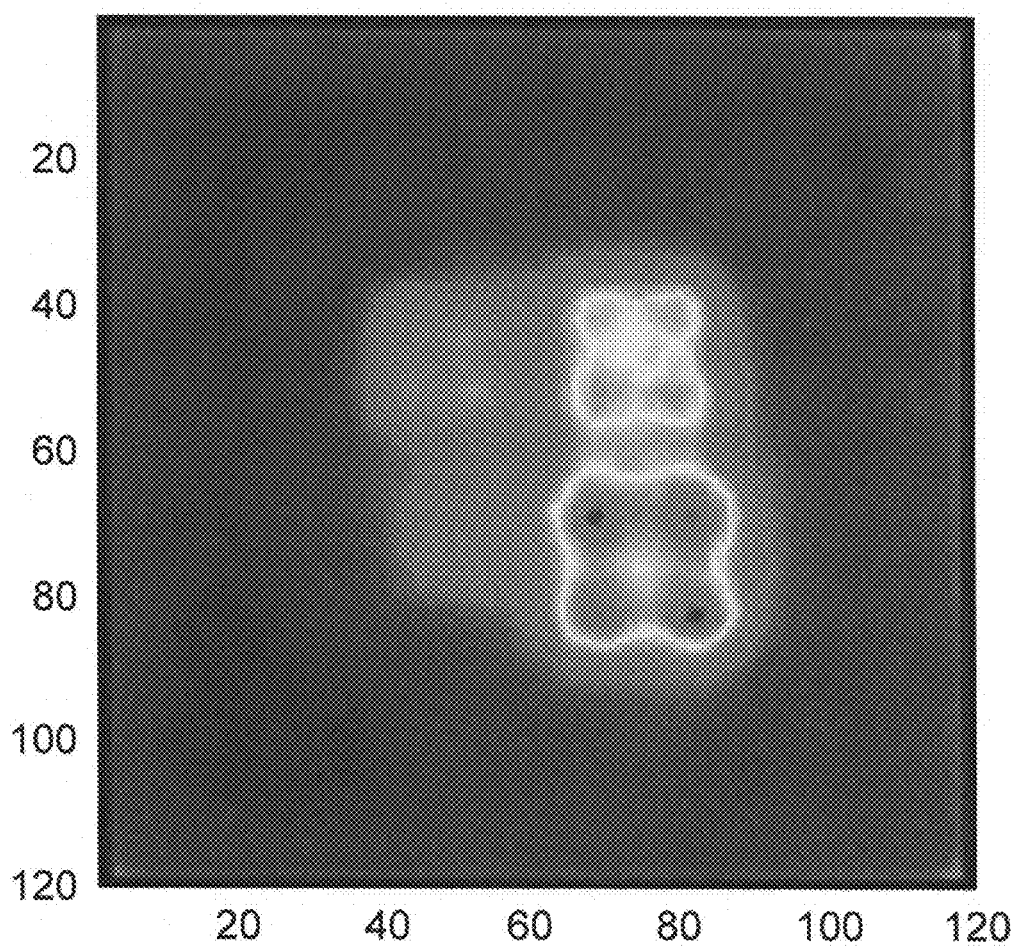

The scatter coincidence events in a 450-570 keV window were reconstructed and compared against a reconstructed image using Compton kinematics collimation of photopeak single photons. The results are shown in FIGS. 13A-B. The scatter fraction for this simulated system was very low due to the 2 cm axial length. Consequently, there were significantly more single photons in the photopeak than scattered coincidences with one photon per pair having energy within the scatter energy window. The difference in reconstructed spatial resolution is still evident in FIGS. 13A-13B. As expected, reconstruction of scatter coincidence events produced higher resolution images than Compton kinematics collimation. Using profiles drawn through the spheres, the FWHM of Gaussian fits were measured to be 5.2-5.8 mm for the reconstructed singles data using Compton kinematics and 4-4.8 mm for scatter reconstruction.

Generally, methods and systems of the present invention can reconstruct single-scatter coincidence events, where one photon from each coincidence photon event underwent scatter in tissue. Methods and systems of the present invention have the capability to improve accuracy of PET systems. Conventional PET systems are limited to imaging true coincidences. In human patients, the scatter fraction is typically 50% of more of the coincidence events. Methods and systems of the present invention can allow these scatter coincidences to be used to reconstruct images, substantially improving sensitivity, image quality, and/or quantification.

While various embodiments of the present invention have been shown and described, it should be understood that other modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

What is claimed is:

1. In an imaging system including a plurality of 3-D detectors, a method for determining a location of a photon event, the photon event producing a photon pair, the method comprising:
   for one of the photons in the photon pair, detecting an interaction in a first 3-D detector, at least one photon of the photon pair being scattered prior to interacting with said plurality of 3-D detectors;
   for the other of the photons in the photon pair, detecting at least two interactions in a second 3-D detector;
   producing a cone-surface projector function based on the at least two interactions in the second 3-D detector;
   producing a projector function based on said produced cone-surface projector function, the detected interaction in the first 3-D detector, and the at least two detected interactions in the second 3-D detector.

2. The method of claim 1, wherein the at least two detected interactions in the second 3-D detector occur in 3-D space within the second 3-D detector.

3. The method of claim 1, wherein the cone-surface projector function provides a set of locations for the photon event at which a probability is greater than zero.

4. The method of claim 1, wherein each of the detected interaction in the first 3-D detector and the at least two detected interactions in the second detector provide an interaction location and energy.

5. The method of claim 1, wherein the photon event is one of a plurality of photon events, and wherein the method further comprises:
   for each of the plurality of photon events, producing a projector function, wherein a plurality of projector functions are produced;
   generating an image based on the plurality of projector functions.

6. The method of claim 1, wherein said produced projector function comprises a single scatter projector function, said single scatter projection function being based on the produced cone-surface projector function;
   generating an image based on the produced single scatter projector function;
   wherein the single scatter projector function is defined at least in part by a volume defined by the produced cone-surface projector function and by a volume enclosed by a single scatter surface.

7. The method of claim 6, wherein the single scatter surface is produced using the detected interaction in the first 3-D detector and at least one of the detected interactions in the second 3-D detector.

8. An imaging system for performing the method of claim 1.

9. An image generator configured to perform the method of claim 1.

10. A computer-readable medium comprising computer-readable instructions that, when read, cause a computer to perform the method of claim 1;
   wherein the computer comprises a processor and memory;
   wherein said detecting an interaction from one photon in a pair in a first 3-D detector comprises the computer receiving signals from the first 3-D detector including an interaction location and energy and processing the received signals;
   wherein said detecting the other photon in the pair produces at least two interactions in a second 3-D detector comprises the computer receiving signals from the second 3-D detector including at least two interaction locations and at least two energies; and wherein the method further comprises:
generating an image from the detected interactions and the detected at least two interactions; and
displaying said generated image on an output device.

11. An imaging method comprising:
within a predetermined time window, receiving at least one signal from each of a pair of 3-D detectors, the signal indicating a photon interaction within the 3-D detector;
for each of the pair of 3-D detectors, determining a combined energy of the at least one signal;
if the combined energy for both of the pair of 3-D detectors is within a first energy window, generating a line projector function based on the received at least one signal from each of the pair of 3-D detectors;
if the combined energy is within a second energy window for one of the pair of 3-D detectors and within the first energy window for the other of the pair of 3-D detectors, generating a projector function based on the received at least one signal from each of the pair of 3-D detectors, wherein the received at least one signal comprises at least two signals from one of the pair of 3-D detectors;
wherein said generating a projector function comprises generating a cone-surface projector function based on the at least two signals from one of the pair of 3-D detectors and generating the projector function based on the generated cone-surface projector function and the received at least one signal from the pair of 3-D detectors.

12. A system for producing an image comprising:
a plurality of 3-D detectors disposed to receive emitted photons from a source, said plurality of 3-D detectors being configured to generate a signal in response to a photon interaction;
an image generator coupled to said plurality of 3-D detectors for producing an image based on the generated signal;
wherein, for an emitted pair of photons in coincidence in which one of the photons in the photon pair is scattered prior to interacting with the plurality of 3-D detectors, the emitted pair of photons generating an interaction signal in a first 3-D detector and at least two interaction signals in a second 3-D detector, said image generator is configured to produce a cone-surface projector function based on the at least two interaction signals in the second 3-D detector;
said image generator being further configured to produce a projector function based on the produced cone-surface projector function, the interaction signal from the first 3-D detector, and the at least two interaction signals in the second 3-D detector.

13. The system of claim 12, wherein said plurality of 3-D detectors comprise cadmium-zinc-telluride (CZT) detectors.

14. The system of claim 13, wherein said CZT detectors are disposed edge-on with respect to the source.

15. The system of claim 14, further comprising:
a source of emitted photons.

16. The system of claim 12, wherein said image generator comprises a computer.

17. The system of claim 12, wherein said image generator is configured to produce a plurality of projector functions, and generate an image based on the plurality of projector functions.

18. A method for producing an image using a single-scatter coincidence photon event, the single-scatter coincidence photon event producing a pair of photons, the method comprising:
for each of the photons in the photon pair, detecting at least one interaction in a 3-D detector, each of the interactions providing a 3-D position and energy;
for at least one of the photons in the photon pair, detecting an additional interaction in the 3-D detector providing a 3-D position and energy;
based on the detected interaction for both of the photons and the detected additional interaction, producing the image;
wherein said producing the image comprises:
determining that the single-scatter coincidence photon event has occurred;
generating a cone-surface projector function based on the provided 3-D position and energy for the interaction and the additional interaction for the at least one of the photons;
generating a projector function based on the generated cone-surface projector function and the at least one detected interaction for each of the photons in the photon pair.

19. A system for radiation-based imaging comprising:
a plurality of 3-D detectors disposed with respect to a source of emitted photons to receive the emitted photons and produce interactions;
an image generator coupled to said plurality of 3-D detectors to receive a position and energy for the produced interactions and reconstruct an image;
said image generator being configured to reconstruct an image using at least one single-scatter coincidence photon event.

* * * * *

UNITED STATES PATENT AND TRADEMARK OFFICE
CERTIFICATE OF CORRECTION

PATENT NO. : 7,888,651 B2  
APPLICATION NO. : 12/154261  
DATED : February 15, 2011  
INVENTOR(S) : Garry Chinn et al.

Page 1 of 1

It is certified that error appears in the above-identified patent and that said Letters Patent is hereby corrected as shown below:

In the Specification:

Col. 1, lines 19-22    Please delete "This invention was made with Government support under contracts EB003283 and CA119056 awarded by the National Institutes of Health. The Government has certain rights in the invention." and insert --This invention was made with Government support under contracts CA119056 and EB003283 awarded by the National Institutes of Health. The Government has certain rights in the invention.-- therefor.

Signed and Sealed this  
Tenth Day of May, 2016

Michelle K. Lee  
*Director of the United States Patent and Trademark Office*